(12) United States Patent
Fair et al.

(10) Patent No.: US 9,408,653 B2
(45) Date of Patent: Aug. 9, 2016

(54) ELECTRIC RATCHET FOR A POWERED SCREWDRIVER

(71) Applicant: Medtronic Xomed, Inc., Jacksonville, FL (US)

(72) Inventors: Christopher L. Fair, Jacksonville, FL (US); Michael L. Koltz, Jr., Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 184 days.

(21) Appl. No.: 14/336,289

(22) Filed: Jul. 21, 2014

(65) Prior Publication Data

US 2014/0327382 A1    Nov. 6, 2014

Related U.S. Application Data

(63) Continuation of application No. 13/095,600, filed on Apr. 27, 2011, now Pat. No. 8,786,233.

(51) Int. Cl.
| | |
|---|---|
| *H02K 17/32* | (2006.01) |
| *H02K 23/68* | (2006.01) |
| *H02K 27/20* | (2006.01) |
| *A61B 17/88* | (2006.01) |
| *B25B 13/46* | (2006.01) |
| *B25B 21/00* | (2006.01) |
| *B25B 15/04* | (2006.01) |

(Continued)

(52) U.S. Cl.
CPC ............ *A61B 17/8875* (2013.01); *B25B 13/46* (2013.01); *B25B 13/461* (2013.01); *B25B 15/04* (2013.01); *B25B 21/004* (2013.01); *H02P 6/22* (2013.01); *H02P 25/021* (2013.01)

(58) Field of Classification Search
CPC .. A61B 17/8875; B25B 13/46; B25B 13/461; B25B 21/004
USPC ................................. 318/434, 400.38, 400.39
See application file for complete search history.

(56) References Cited

U.S. PATENT DOCUMENTS

| | | | |
|---|---|---|---|
| 3,734,207 | A | 5/1973 | Fishbein |
| 4,289,131 | A | 9/1981 | Mueller |
| 4,441,563 | A | 4/1984 | Walton, II |

(Continued)

FOREIGN PATENT DOCUMENTS

| | | |
|---|---|---|
| EP | 2221022 A1 | 8/2010 |
| GB | 2171343 A | 8/1986 |

(Continued)

OTHER PUBLICATIONS

Office Action for Korean Patent Application No. 10-2013-7030643 dated Feb. 3, 2015.

(Continued)

*Primary Examiner* — Erick Glass
(74) *Attorney, Agent, or Firm* — Harness, Dickey

(57) ABSTRACT

A powered screwdriver system includes an electric ratchet. In accordance with one aspect, the powered screwdriver system includes a driver housing and includes a motor disposed within the housing. A working end provides a rotational output and is mechanically coupled to the rotor. A power source provides power to the motor. A controller receives signals representative of a motor condition and, based on the received signals, controls the motor in a manner providing the electric ratchet.

25 Claims, 4 Drawing Sheets

(51) Int. Cl.
*H02P 6/22* (2006.01)
*H02P 25/02* (2016.01)

(56) References Cited

U.S. PATENT DOCUMENTS

| | | | |
|---|---|---|---|
| 4,473,226 A | 9/1984 | Siegel et al. |
| 4,728,876 A | 3/1988 | Mongeon et al. |
| 4,873,461 A | 10/1989 | Brennan et al. |
| 5,080,983 A | 1/1992 | Alexon et al. |
| 5,115,175 A | 5/1992 | Fletcher |
| 5,136,220 A | 8/1992 | Philipp |
| 5,136,469 A | 8/1992 | Carusillo et al. |
| 5,196,015 A | 3/1993 | Neubardt |
| 5,207,697 A | 5/1993 | Carusillo et al. |
| 5,264,783 A | 11/1993 | Vig et al. |
| 5,268,622 A | 12/1993 | Philipp |
| 5,309,714 A | 5/1994 | Putney et al. |
| 5,365,155 A | 11/1994 | Zimmermann |
| D364,463 S | 11/1995 | Pitzen et al. |
| 5,474,558 A | 12/1995 | Neubardt |
| 5,553,675 A | 9/1996 | Pitzen et al. |
| 5,625,273 A | 4/1997 | Fehling et al. |
| 5,670,749 A | 9/1997 | Wieloch et al. |
| 5,697,158 A | 12/1997 | Klinzing et al. |
| 5,712,543 A | 1/1998 | Sjostrom |
| 5,747,953 A | 5/1998 | Philipp |
| 5,766,793 A | 6/1998 | Kameishi et al. |
| 5,792,573 A | 8/1998 | Pitzen et al. |
| 5,804,936 A | 9/1998 | Brodsky et al. |
| 5,903,423 A | 5/1999 | Okano et al. |
| 6,199,642 B1 | 3/2001 | Becker et al. |
| D534,651 S | 1/2007 | Bruce et al. |
| RE40,681 E | 3/2009 | Pitzen et al. |
| RE40,848 E | 7/2009 | Pitzen et al. |
| 7,677,844 B2 | 3/2010 | Schell et al. |
| 8,786,233 B2 | 7/2014 | Fair et al. |
| 2004/0217727 A1 | 11/2004 | Gilmore |
| 2004/0220602 A1 | 11/2004 | Deng et al. |
| 2004/0243207 A1 | 12/2004 | Olson et al. |
| 2004/0254575 A1 | 12/2004 | Obenchain et al. |
| 2005/0004623 A1 | 1/2005 | Miles et al. |
| 2005/0268750 A1 | 12/2005 | Bruce et al. |
| 2009/0299439 A1 | 12/2009 | Mire et al. |
| 2009/0308628 A1 | 12/2009 | Totsu |
| 2011/0030981 A1 | 2/2011 | Totsu |
| 2012/0274253 A1 | 11/2012 | Fair et al. |

FOREIGN PATENT DOCUMENTS

| | | |
|---|---|---|
| JP | S62-102977 A | 5/1987 |
| JP | 2004-082222 A | 3/2004 |
| JP | 2009072888 A | 4/2009 |
| JP | 2012-030325 A | 2/2012 |
| KR | 2010-0111821 A | 10/2010 |
| WO | WO-2012-014503 A1 | 2/2012 |

OTHER PUBLICATIONS

Patent Examination Report No. 1 dated Apr. 9, 2015 for Australian Patent Application No. 2012249830.
International Preliminary Report on Patentability and Written Opinion mailed Nov. 7, 2013 for PCT/US2012/035004 claiming benefit of U.S. Appl. No. 13/095,600, filed Apr. 27, 2011.
JP Office Action for Japanese Patent Application No. 2014-508517 which corresponds to PCT/US2012/035004 with English Translation dated Mar. 18, 2016.
US 2005/0025703 A1, 02/2006, Miles et al. (withdrawn)

ELECTRIC RATCHET FOR A POWERED SCREWDRIVER

CROSS-REFERENCE TO RELATED APPLICATIONS

This application is a continuation of U.S. patent application Ser. No. 13/095,600 filed on Apr. 27, 2011. The entire disclosure of the above application is incorporated herein by reference.

FIELD

The present invention relates generally to the field of screw driving systems, and more particularly to screw driving systems having ratcheting systems.

BACKGROUND

This section provides background information related to the present disclosure which is not necessarily prior art.

Powered screwdrivers are much more efficient than manual screwdrivers for driving screws and bolts. However, without exercising great care, powered screwdrivers can over-tighten or over-rotate screws or bolts. In some critical applications, such as in surgical applications, users may drive screws manually to avoid over tightening or to orient a driven screw or bolt at a desired rotational position. In these instances, a user may drive a screw with a powered driver until the screw begins to approach the critical location. Then, in order to reduce the chance of over-tightening or over-rotating, the user may set aside the powered driver and manually tighten the screw with a separate ratchet or a manual screwdriver.

Ratchets are more efficient than manual screwdrivers for tightening screws or bolts because they prevent rotation in the driving direction and provide continuous freewheel rotation in the other. Accordingly, ratchets are often preferred over manual screwdrivers in surgical applications. Conventional ratchets use mechanical assemblies between the handle of a driving tool and the hardware being driven. For example, conventional mechanical ratchet assemblies include gear systems, high friction surfaces with pawls, sprockets with teeth and pawls, or sprags to mechanically limit rotation in one direction.

These conventional ratchets require large mechanical assemblies that increase both the size of the overall tool and increase the overall weight. For example, ratchet housings must be sized to accommodate the mechanical ratchetings systems. In addition, these mechanical assemblies add mass to the ratchet and subsequently, add additional inertia to the rotating components of the tool. Larger, heavier systems may increase operator fatigue and/or operator injury, potentially resulting in less effective screw targeting. This may affect the patient's surgical outcome.

The device and methods disclosed herein overcome one or more of the shortcomings discussed above and/or in the prior art.

SUMMARY

This section provides a general summary of the disclosure, and is not a comprehensive disclosure of its full scope or all of its features.

The present disclosure is directed to powered screwdriver system having an electric ratchet.

In accordance with one aspect, the present disclosure is directed to a powered screwdriver system that includes a driver housing having a handle portion configured for gripping by a user and includes a motor disposed within the housing. The motor includes a stator and a rotor with the rotor rotationally disposed within the stator. A working end provides a rotational output and is mechanically coupled to the rotor. A power source provides power to the motor. A controller receives signals representative of a motor condition and, based on the received signals, controls the motor in a manner providing an electric ratchet capability.

In one aspect, the controller is configured to receive signals indicative of a location of the rotor relative to the stator and is configured to power the motor to maintain a desired position of the rotor relative to the stator in a first direction. In another aspect, the controller is configured to permit freewheel rotation of the rotor relative to the stator in a second direction opposite the first direction.

In another exemplary aspect, the present disclosure is directed to a powered screwdriver system having a handpiece driver and a control console. The handpiece driver comprises a housing having a handle portion configured for gripping by a user and a motor disposed within the housing. A working end provides a rotational output and is mechanically coupled to the rotor. The control console is separate from and in electrical communication with the handpiece driver. It comprises a controller configured to commutate the motor to maintain a desired relative position of the rotor within the stator when loading is applied in a first direction on the motor, the controller also being configured to permit freewheel displacement of the rotor within the stator when loading is applied in a second direction on the motor.

In one aspect, the controller is configured to receive signals indicative of a position of the rotor relative to the stator and is configured to determine the desired relative position of the rotor based on the signals.

In another exemplary aspect, the present disclosure is directed to a method of operating a surgical screwdriver system. The method includes steps of estimating a starting rotor position relative to a stator and setting a first desired rotor position relative to the stator that is substantially equivalent to the starting rotor position. The method also includes steps of commutating the motor to substantially maintain the first desired rotor position relative to the stator and offset loading on the rotor applied in a first direction. Displacement of the actual rotor position within the stator is permitted in response to loading applied on the rotor in a second direction. The method also includes setting a second desired rotor position relative to the stator that is substantially equivalent to the displaced rotor position.

In one aspect, the method includes determining an error factor as a difference between the first desired rotor position and the actual rotor position and performing the step of commutating the motor to substantially maintain the first desired rotor position when the error factor exceeds a preestablished threshold value. In one aspect, the method includes determining an error factor as a difference between the first desired rotor position and the actual rotor position and performing the step of setting a second desired rotor position when the desired rotor position is positive and the error factor is negative or when the desired rotor position is negative and the error factor is positive.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
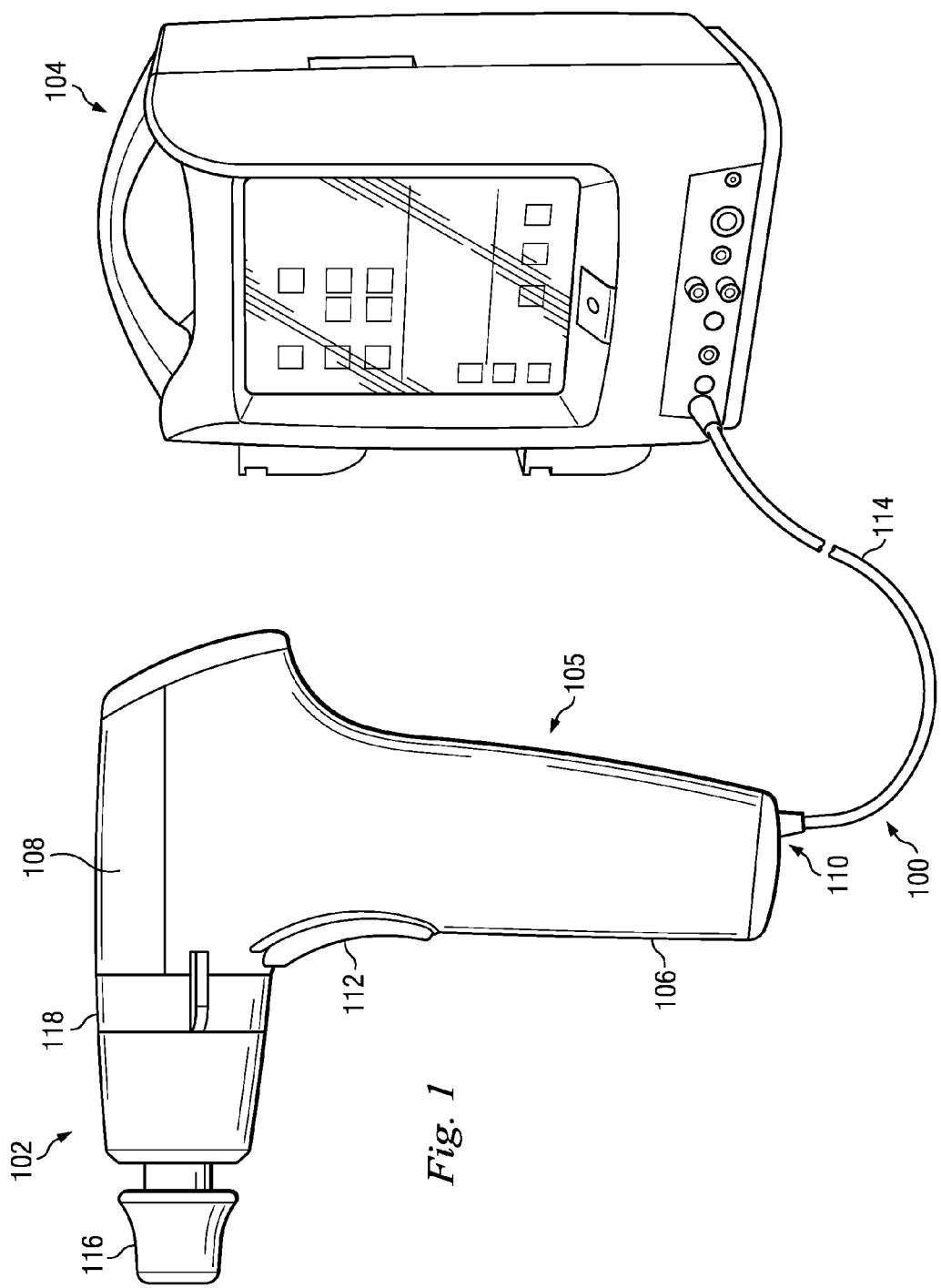
FIG. 1 is an illustration of an exemplary motor powered screwdriver system including a driver and a control console and provided with an electric ratchet in accordance with a first embodiment of the present disclosure.

Example embodiments will now be described more fully with reference to the accompanying drawings.

For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

This disclosure describes a motor-driven powered screwdriver system with an electric ratchet. The system controls the motor to create a ratchet by preventing or limiting relative rotation of the powered driver and a driven screw in one direction, while permitting freewheel rotation in the other. Particularly, to drive a screw using the electric ratchet, the screwdriver system detects displacement of motor components and responds by powering the motor to limit or prevent further displacement. Accordingly, when motor displacement beings to occur as a result of manually applied torque, the motor is powered to offset the displacement effectively limiting the driver from slipping relative to the screw in one direction. However, the motor effectively permits freewheel rotation in the second direction. Accordingly, by rotating the whole driver relative to the driven screw, a user can ratchet and drive the screw to a desired depth and orientation. As used herein, freewheel rotation is intended to encompass at least two scenarios: First, freewheel rotation occurs when the motor is not powered to prevent motor displacement in the second, opposite direction; and second, freewheel rotation occurs when the motor is powered to offset drive train drag when the motor is rotated in the second opposite direction.

The powered screwdriver system is particularly well suited for surgical applications where the driver is used to drive bone screws, such as pedicle screws. The user can use the motor powered driver to drive the screw to near its desired depth. In order to reduce the risk of over tightening or over driving however, the user can stop conventional driving with the motor and use the driver as a ratchet to complete the screw implantation to the desired torque or depth. In addition, as some bone screws, such as some pedicle screws, must be oriented to receive spinal rods, cables, or other medical instrumentation, the electric ratchet allows the fine adjustment necessary for aligning the screw as desired without detaching the driver from the screw and without requiring a separate ratchet or manual screwdriver. This increases surgical efficiency and convenience for the surgeon. In addition, since the electric ratchet lacks large, heavy mechanical ratchet components, the resulting ratcheting screwdriver does not increase operator fatigue or potential operator injury. This may lead to more effective screw targeting and improved patient outcome.

Furthermore, because the electrical ratcheting system operates using motor control instead of bulky mechanical components, the systems disclosed herein achieve ratcheting operation without adding additional mass and weight. By avoiding the additional mass, the drivers disclosed herein do not have the extra inertia that comes from the mechanical systems, making the driver more efficient. This enables a compact size and minimizes driver weight, which are important benefits to an operating surgeon.

FIG. 1 illustrates a powered screwdriver system 100 according to an exemplary embodiment of the present invention. The system includes a motor powered driver 102 and a control console 104. The driver 102 operates at variable rotational velocities to drive taps, drill bits, and surgical hardware, such as, for example, bone screws during a surgical procedure. In addition to performing these functions using motor power, the driver 102 is configured with an electric ratchet. The driver 102 includes an outer housing 105 in the shape of a handle 106 and a barrel 108. Here, the handle 106 extends from the barrel 108 in a pistol-grip fashion for convenience and comfort of the user. The handle 106 includes an electrical port 110 and an input device, here shown as a trigger 112. In some examples, the trigger 112 includes a permanent magnet and a Hall effect sensor. In use, the magnetic field detected by the Hall effect sensor changes based on the relative position of the trigger 112 and the proximity of the magnet within the trigger to the Hall effect sensor.

The barrel 108 includes a collet 116 and a mode selector 118. Other input devices, such a torque control level or limit, alignment elements, and other features also may be included. The collet 116 is disposed at the working end of the driver 102 and receives a tool, such as a tap, drill bit, driver, socket, or other tool. The mode selector 118 is arranged to control the driving direction of the driver 102. In some examples, the available modes include a forward mode, a reverse mode, an oscillating mode, a lock or non-rotation mode, among other modes. By switching the mode selector 118, a user can control the rotational driving direction of the collet 116. In the example shown, the mode selector 118 is a collar disposed about a portion of the barrel 108. In other embodiments, the mode selector 118 is a button, a toggle lever, a rocker switch, or other input device.

The driver 102 contains a motor for driving the tools at the working end. In some examples, the motor is a brushless DC motor configured to be powered from the control console 102. In these examples, the electrical port 110 connects the driver 102 with the control console 104 through the cable 114. In other examples, the driver and console communicate wirelessly. In one example, the handle 106 of the driver 102 contains a motor disposed so that the motor shaft extends upwardly from the handle 106 into the barrel 108. A gear mechanism connects the motor shaft to a substantially horizontally extending driving shaft connected to the collet 116 and that is utilized to drive a drilling tool or mechanized end received by the driver 102.

Figure 2:
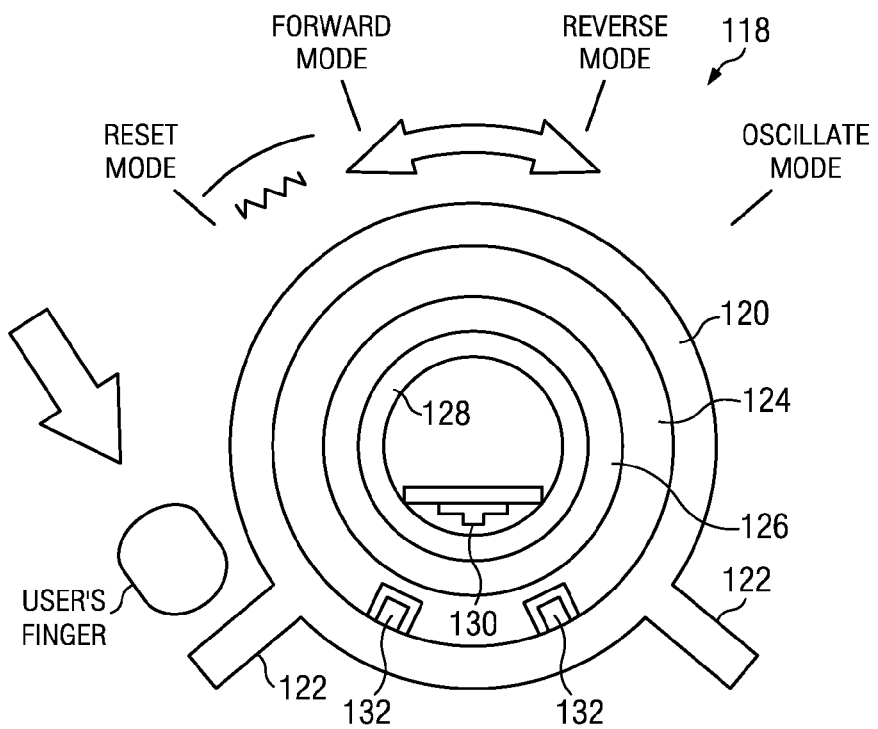
FIG. 2 is an illustration of a highly simplified cross-sectional view of a mode selector on the exemplary driver of FIG. 1.

One example of the mode selector 118 is shown in greater detail in FIG. 2. Here, the mode selector 118 includes a collar 120 that includes radially projecting tabs 122 that enable a user to easily rotate the mode selector about a central axis to change driving modes. A magnet ring 124 is fixed to and rotates with the collar 120. The magnet ring 124 and collar 120 are disposed on a portion of the body 126 of the driver barrel 108, with an insulating layer 128 and Hall effect sensor 130 disposed therein. The magnet ring 124 includes a plurality of magnets 132. Rotation of the mode selector 118 displaces the magnets 132 relative to the Hall effect sensor 130. The Hall effect sensor 130 generates a signal used to identify the position of the mode selector 118, and likewise, to identify the selected mode. In the embodiment shown, the mode selector 118 may communicate a signal representing the mode or the position of the collar to the control console 104. Other examples of mode selectors include a single magnet 132 and multiple hall effect sensors 130. Other types of sensors are contemplated as being used in place of the Hall effect sensors including, for example, reed sensors and others.

The mode selector enables a user to select the operating mode of the driver 102. In the example shown, the available modes include a forward mode, a reverse mode, an oscillating mode, and a lock or non-rotation mode, among other modes. Some designs provide ancillary user inputs not related to shaft control. The location of the magnets relative to the Hall effect sensors provides an indication of the selected mode. This is communicated back to the console 104 for processing and functional implementation.

Returning to FIG. 1, the control console 104 may include controls and settings for operating the driver 102. In one example, the control console 104 is configured to receive signals from the driver 102 and control the output of the driver 102 based on those received signals, combined with user settings received directly at the control console. Some examples of this may become apparent from the description below. It is worth noting that some systems do not include a separate control console, and in such embodiments, all determinations and calculations may be performed elsewhere, such as for example, onboard the driver 102 itself.

Figure 3:
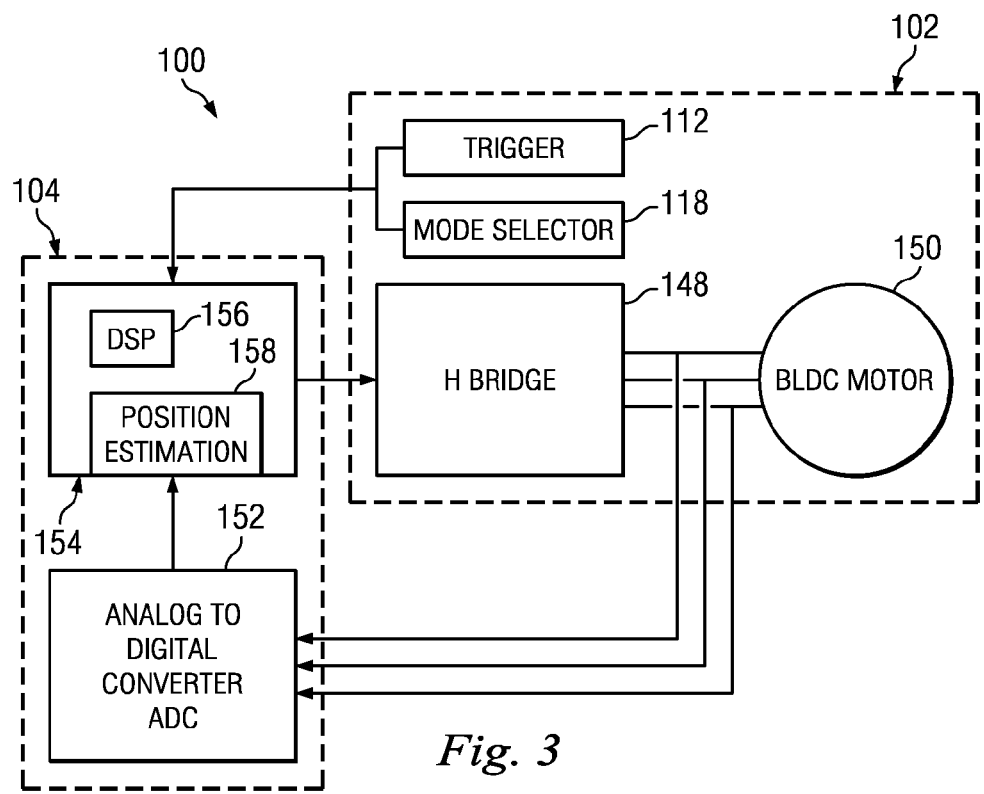
FIG. 3 is a block diagram showing functional components of the motor powered screwdriver system with an electric ratchet in accordance with one aspect of the present disclosure.

FIG. 3 shows a block diagram of one example of a system 100 in accordance with an exemplary aspect of the present disclosure. As can be seen, the system includes the driver 102 and the control console 104. In this example, the driver 102 includes the trigger 112, the mode selector 118, an H-bridge 148, and a motor 150.

The H-bridge 148 directs power from the control console 104 to the motor 150. Depending on the operating mode determined by the mode selector 118, the H-bridge directs power in one direction or the other. For example, if the mode selector 118 is changed from forward mode to reverse mode, the H-bridge redirects power through the motor and switches its operating direction.

Figure 4:
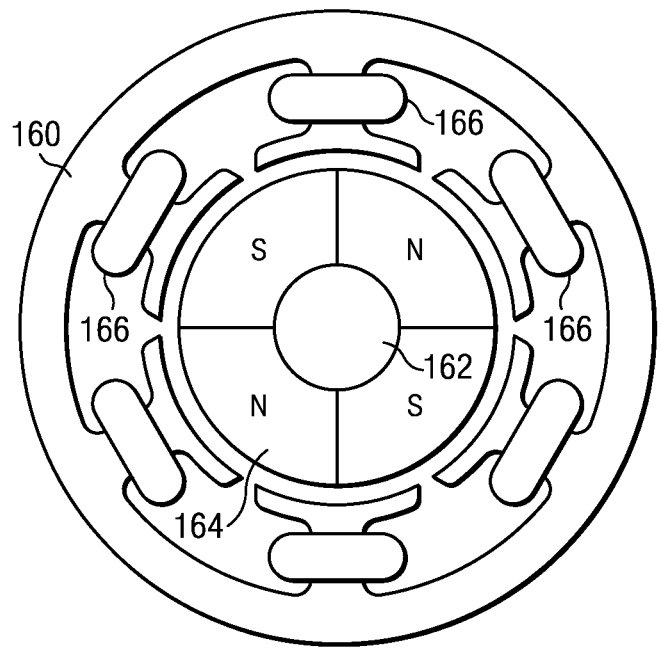
FIG. 4 is a stylized illustration of a cross-sectional view of an electric motor in accordance with an exemplary aspect of the present disclosure.

In this example, the motor 150 is a brushless DC motor having three windings represented by the three inputs from the H-bridge 148. FIG. 4 shows a stylized example of a brushless DC motor in accordance with one aspect of the present disclosure. The motor 150 in FIG. 4 is a synchronous motor and includes a stator 160, a rotor 162, and permanent magnets 164 disposed on and rotatable with the rotor 162. In this example, the motor is a 3-phase motor, although 2-phase and single phase motors may be used in other embodiments. The stator 160 includes windings 166. In this example, the magnets 164 include two pole pairs with alternate north and south poles. Thus, the example shown is a four pole motor. However, in another example, only a single pole pair motor, or two pole motor, is used. Other embodiments include substantially more pole pairs. Some examples have up to eight pole pairs or more, with the more pole pairs being present, the more exact control can be determined. As in conventional motor systems, the rotor 162 rotates relative the stator 160. The stator is fixed relative to the driver housing 105. Accordingly, when a user physically turns the driver to effect a manual driving of a screw, the stator 160 stays fixed relative to the driver housing 105. In some examples, the motor has a motor housing about the stator 160 fixed in place relative to the driver housing 105.

Returning to FIG. 3, the control console 104 includes a processing system and memory programmed such that the control console 104 is configured to receive various setting inputs from a user (e.g., maximum speed and maximum torque) and to control the motor of the driver 102 based on the user's setting inputs and depression of the trigger 112 on the driver 102. In that regard, the control console 104 of the system 100 provides position control and torque control to the motor of the driver 102.

In this example, the control console 104 includes an analog to digital converter (ADC) 152 and a controller 154 that comprises a processor 156 running a position estimation module 158. The system 100 also includes memory containing executable programs that influence the manner in which the system 100 operates, a user interface, communication modules, and other standard equipment. In some examples using the control console 104, a user is able to set the maximum speed, acceleration, jerk, and mode (forward, reverse, or oscillate) for the system. Further, the processor 156 receives a signal indicative of the amount of depression of the trigger 112. The signal sent to the processor 156 may be indicative of the amount of trigger depression based on the magnetic field sensed by the Hall effect sensor, as indicated above. Also, as indicated above, all signal communication between the driver and the console may be over the cable 114. Alternatively, communication may be wireless Bluetooth, Wi-Fi, conventional RF, infrared, or other communication method.

In the example shown, the processor 156 is a digital signal processor that receives the various setting inputs from the user. Based on the settings, and particular pre-stored executable programs, the processor controls the H-bridge and sends signals to the H-bridge, which are communicated to the motor 150. For example, using the inputs received with respect to the maximum speed, acceleration, jerk, mode, and trigger position, the controller 154 drives the position of the rotor of the driver 102. The controller 154 outputs a pulse-width modulated control signal that has a duty cycle in accordance with a desired control curve to control the position of the rotor of the motor.

In this example, the control console 104 uses the back electromotive force (EMF) from the motor 150 to monitor the rotor position of the motor 150 to ensure that the motor's rotor is achieving the desired positions defined by the control curve. This is accomplished by detecting the EMF level for each winding in its turn at the controller 154. The EMF signals are sent from the motor to the ADC, which converts the EMF signals to digital signals, which are then communicated to the controller 154. During standard operation, if the rotor is not achieving the desired positions (e.g., the rotor has rotated too far or not far enough) as detected by the EMF, then the controller 154 adjusts the duty cycle based on an error signal representative of the difference between the actual position of the rotor and the desired position of the rotor. In this manner, the system 100 monitors the position of the rotor to ensure that the rotor is achieving the desired positions during use of the driver 102.

In the driver 102, the stator 160 (FIG. 4) is fixed in place relative to the driver housing 105 (FIG. 1). The motor rotor 162 is at least rotatably, mechanically coupled to the drive shaft and collet 116 either directly or through a gear system, for example. Therefore, movement of the rotor 162 relative to the stator 160 is indicative of movement of the collet 116 (and a tool in the collet) relative to the driver housing 105. Accordingly, when the collet 116 and the drive shaft are engaged with a tool, which may be engaged to a screw, the system 100 can detect relative movement between the screw and the driver 102. In this example, the controller 154 of the system 100 is configured to operate the electric ratchet by receiving data, such as EMF indicative of the rotor position relative to the stator and applying power to the motor at a level sufficient to reduce or prevent further detected relative movement between the rotor and the stator.

Figure 5:
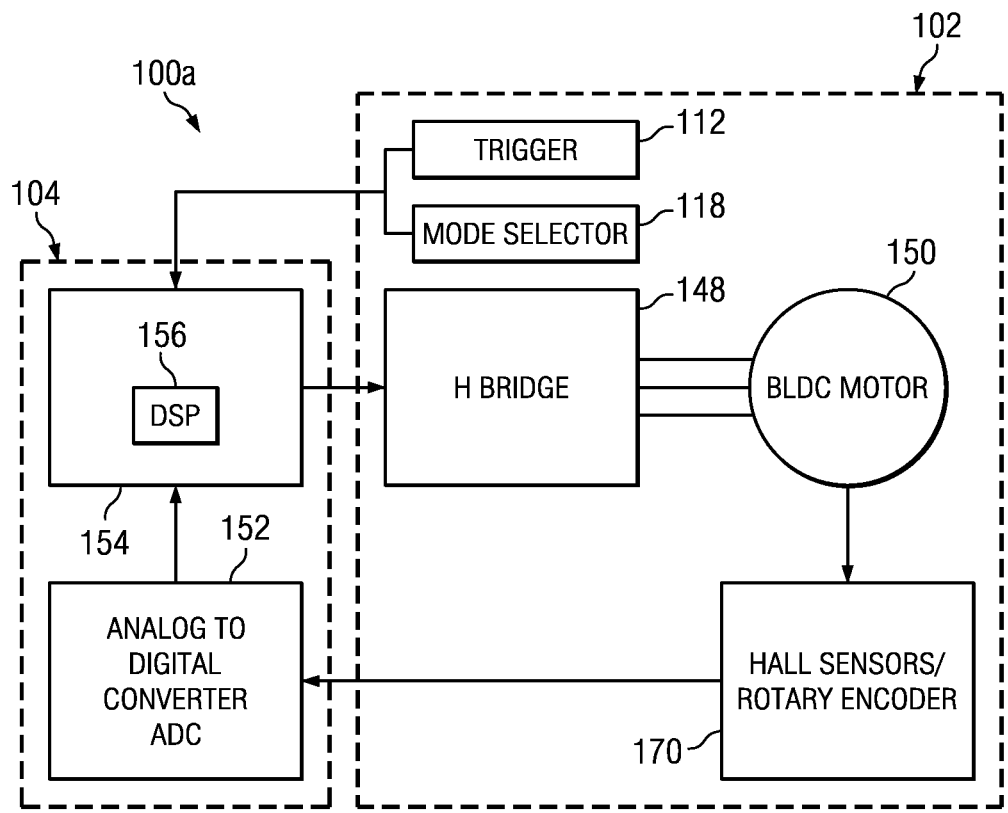
FIG. 5 is a block diagram showing functional components of the motor powered screwdriver system with an electric ratchet in accordance with one aspect of the present disclosure.

FIG. 5 shows a block diagram of an example of a system 100a in accordance with another exemplary aspect of the present disclosure. As can be seen, the system 100a includes the driver 102 and the control console 104. In this example, the driver 102 includes the trigger 112, the mode selector 118, the H-bridge 148, and the motor 150. However, this embodiment also includes a position sensing element 170. The position sensing element 170 may be any device configured to directly identify the position of the rotor in the motor 150. In one example, the position sensing element 170 is a plurality of Hall effect sensors. In this example, the Hall effect sensors are disposed in the stator of the motor and are configured to detect the passage of the magnetic poles of the rotor and emit a voltage signal that is passed to the control console 104. One example uses three Hall effect sensors. However, greater and smaller numbers of Hall effect sensors are contemplated.

In FIG. 5, the control console 104 includes the ADC 152 and the controller 154. However, here, the controller 154 can receive data directly indicating the position of the rotor, and therefore, the controller need not include a position estimation module 158. As described above with reference to FIG. 3, the ADC 152 converts the voltage signal from the position sensing element 170 to a digital signal and passes it to the controller 154. In this example, instead of determining position as required by the system 100 in FIG. 3, the controller 154 directly detects the position of the rotor relative to the stator. The controller 154 may then operate the motor 150 based on the position of the rotor to prevent or limit freewheel rotation in one direction while permitting freewheel rotation in the other direction, thereby achieving the ratcheting effect. Although described as Hall effect sensors, the position sensing element 170 may also be a rotary encoder or other direct position measuring system that will measure the position of the rotor 162 relative to the stator 160.

Figure 6:
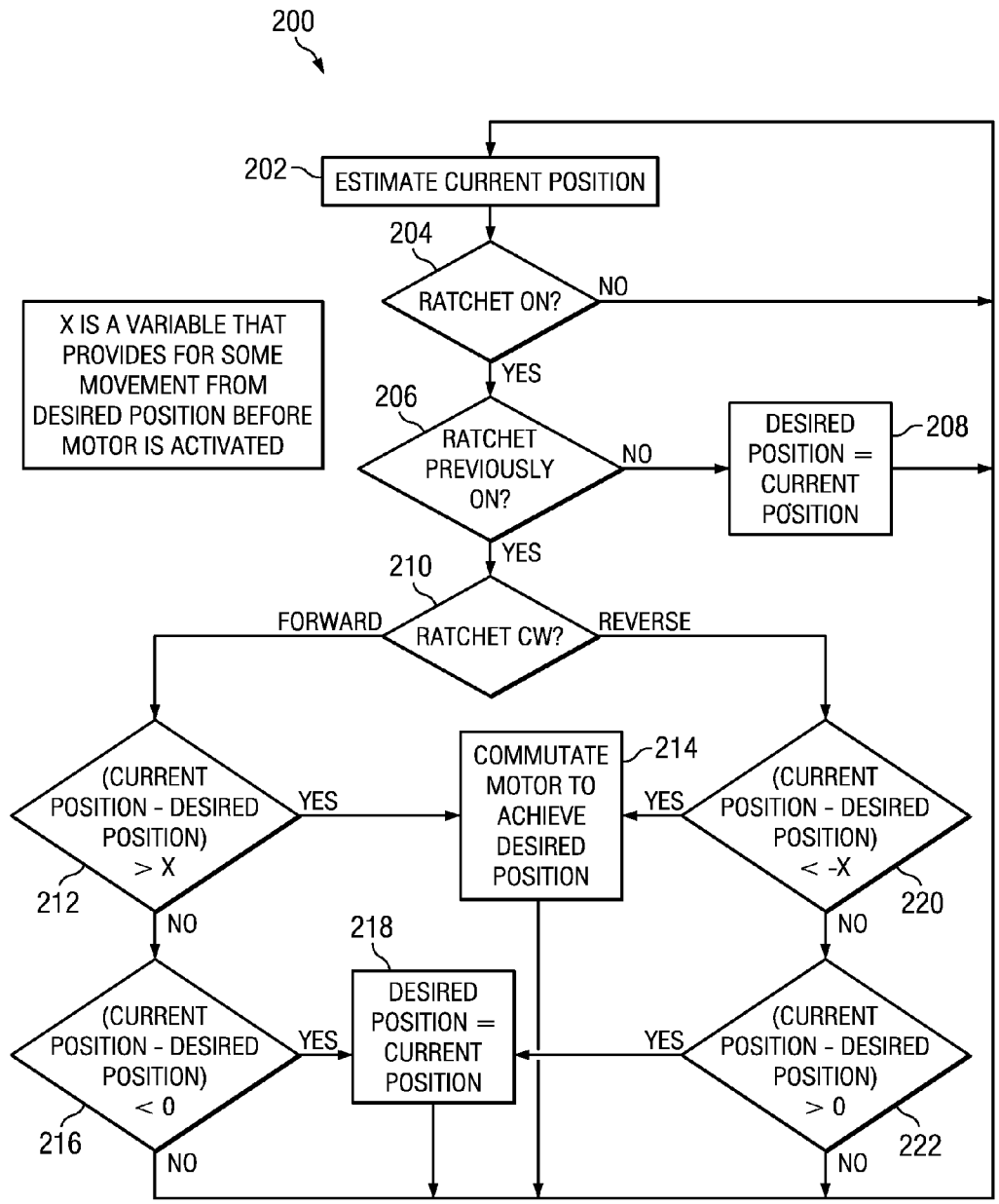
FIG. 6 is a flow chart showing control logic in accordance with one exemplary aspect of the present disclosure.

This is explained further with reference to FIG. 6, which shows a logic flow chart performed by the controller 154 to achieve the electric ratchet functionality of the powered screwdriver system 100. In one example the logic flow chart is an executable program of a method stored in memory and executable by the processor 156. The method, referenced by the numeral 200, begins at a step 202 where the processor 156 estimates the current position of the rotor relative to the stator. This may be accomplished in any of a number of methods, including those methods described above where the controller 154 monitors EMF from the motor 150, and based on the EMF determines the position of the rotor or where the controller 154 receives signals from Hall effect sensors or encoders associated with the motor that indicate the position of the rotor relative to the stator.

At a step 204, the controller determines whether the ratchet mode is on or active. In one example, this is accomplished by detecting the position of the mode selector 118. If the mode selector 118 is at a position where the ratcheting mode is active, then a signal is sent from the driver 102 to the control console 104 for processing by the controller 154. The signal permits the controller to operate the system 100 in a ratcheting mode. In some examples, the signal is the absence of alternative signals. In the mode selector 118 described above, the ratcheting mode is active in a forward direction anytime the mode selector 118 is in a forward mode and the trigger is not depressed. The ratcheting mode is active in a reverse direction anytime the mode selector 118 is in a reverse mode and the trigger is not depressed. In other examples, the mode selector includes a ratcheting mode independent of the forward and reverse modes. Accordingly, a user may activate or turn on the ratchet mode by moving the mode selector to a ratchet mode. Mode selectors may include buttons or switches independent of the mode selector described above, and may be disposed on the console 104 or on the driver 102. If, at step 204, the ratchet mode is not on, then the system cycles in a loop, continuing to estimate the current position of the rotor relative to the current position. In this condition, the driver may still operate in normal functions, permitting forward driving, reverse driving, or oscillating, among other control scenarios.

If at step 204, the ratchet mode is on, then the controller 154 determines whether the ratchet was previously on or whether this is the first time through the loop at a step 206. If it is the first time through the loop at step 206, then the loop sets a desired position of the rotor relative the stator. Here, it sets the desired position as equal to the current position at a step 208. The step of setting the desired position equal to the current position at step 208 uses the current position that was estimated at step 202. With the desired position set at step 208, the process returns to step 202 and again estimates the current position of the rotor relative to the stator. This estimated current position value is stored for later use.

If the ratcheting mode was previously active or on at step 206, then the controller 154 determines whether the ratchet is set for forward (clockwise) or reverse (counterclockwise) rotation at step 210. In some embodiments, the direction of rotation is associated entirely with the setting of the mode selector. For example, if the mode selector is set in a forward mode, then the direction may be set as forward. If the mode selector is set in a reverse mode, then the direction selector may be not set as forward, but instead is set at reverse. In some examples, as indicated above, the system 100 may be configured to ratchet in only a single direction. Accordingly, the direction selector at step 210 may also be a condition for determining whether the ratchet is on and therefore, in some examples may be a part of step 204.

In this example, where the ratcheting may be selected to be forward or reverse, the method continues from step 210 depending on the direction selected. If the direction is forward at step 210, then the method determines the difference between the desired position and the current position last taken at step 202. This difference is referred to herein as an error value. The error value is then compared to a preset threshold value x to determine whether to use the motor to counter applied loading and use the system as a ratchet. The threshold value x is a variable that provides for some movement from the desired position before the motor is activated. In some examples however, the value x is zero or substantially zero.

At step 212, if the error value between the current and the desired positions is greater than the preset value x, then the controller 154 commutates the motor to achieve the desired position at a step 214. Accordingly, as the driver housing begins to displace relative to the collet and driving tool in the driver 102, the error value between the current position and the desired position increases until it exceeds the preset value x. Once the error value is greater than x, the controller 154 controls the motor with power sufficient to effectively offset the torque being applied to maintain the rotor substantially in the desired position relative to the stator. This need not necessarily require bringing the error to zero, but may be include merely limiting or controlling further increases in the error value. Thus, as a user rotates the driver 102 forward without depressing the trigger 122, the motor substantially maintains the rotor position relative to the stator, thereby manually driving the hardware, such as a bone screw. Further, since the threshold value of x may be in micro degrees, the relative displacement may be imperceptible to a user. In one example, the value of x amounts to less than one degree of relative movement.

If at step 212, the error value between the current and desired positions is less than the value of x, then the processor 154 determines at a step 216 whether the error value is less than zero. A value less than zero at step 216 indicates that the rotor 162 is being turned in reverse relative to the stator 160. Consistent with conventional mechanical ratchet operation, freewheel rotation in one direction is permitted while rotation in the other direction is not. Accordingly, in this embodiment, the motor is not controlled to limit or prevent rotation in the reverse direction at step 216. Accordingly, if the error value between the current and desired positions is less than zero, then the controller 254 resets the desired position to the detected current position at step 218. This provides a new starting point (desired position).

If at step 216, the error value between the current and desired position is not less than zero, but was also not greater than x at step 212, then the controller returns to step 202 and begins the process again.

Returning now to step 210, if the ratchet setting were not set for forward ratcheting, then in one example, the controller 154 determines the error value between the current position and the desired position and compares it to a negative value of x (−x) at step 220. Operation then operates in a manner similar to that described above with reference to steps 212, 214, 216, and 218, but using the opposite direction, resulting in a negative x. That is, if the error value is less than negative x, then the controller 154 controls the motor to maintain the current position at the desired position at step 214. As such, the system effectively limits or prevents relative movement of the driver 102 and the collet or a screwdriver in the collet. If the error value between the current and desired positions is not less than negative x, then the controller 154 determines whether the error value is greater than zero at a step 222. If the error value is greater than zero, then at step 218, the desired position it set equal to the current position. If is not greater than zero, then the processor returns to step 202.

The method 200 described in FIG. 4 is for a system that permits ratcheting in both the forward and rearward directions, depending on the setting. Some embodiments permit ratcheting in only one direction, such as a forward driving direction. In such a system, the steps 220 and 222 may be not present. Because the motor is powered to prevent or limit relative movement between the collet and the driver 102, a user can drive the instrument or tool, whether a screw, a tap, a bit or other instrument or tool, by rotating the driver 102 in a forward direction without depressing the trigger.

In one example, the system 100 is configured so that when the driver is manually rotated in the freewheeled rotation direction, the driver 102 or control console 104 emits a clicking sound. For example, the clicking sound may be emitted when the system is in a ratchet mode and the collet displaces relative to the driver body by a preset range of rotation, as measured by the displacement of the rotor relative to the stator. In one embodiment, the controller 154 is configured to generate a signal that results in a clicking noise one time for every ten degrees of freewheeled rotation. The speaker emitting the clicking noise may be disposed on the driver 102 or on the control console 104. Accordingly, users may hear an electronically generated clicking in the same way users may hear a mechanical generated clicking noise in a conventional mechanical system, such as toothed sprocket with pawl systems. In some examples, instead of an audible clicking noise, the PWM of the motor voltage provides audible feedback to the user. For example, as applied shaft torque increases, an audible tone generated by the motor may provide feedback to the user. In some examples, as the torque increases, the volume of the audible tone increases, or alternatively, as the torque increases, the pitch (based on frequencies) increases.

Although shown and described as having both driver and a control console, some embodiments of the present disclosure include a driver containing the processing capability that is disclosed herein as being on the control console 104. Accordingly, in some examples, the controller 154 is disposed on the driver itself. Further, although the embodiment shown discloses operating power being drawn from the control console 104, some driver embodiments include their own separate power source, such as a battery power source, using either a rechargeable battery pack or primary batteries. Some embodiments include a power cord pluggable into a conventional power outlet.

In some examples the driver is a surgical tool configured to be used in a surgical setting. Accordingly, the driver may be configured in a manner to be sterilized by an autoclave. Further, the driver may be configured to be entirely self-contained, without vents or releases of material or filaments from the motor that could introduce contamination to a sterile field.

As described above, the freewheel capability of the electric ratchet includes not powering the motor to prevent motor displacement in the second freewheel direction opposite the first, driving direction. Accordingly, a user can freely rotate the driver relative to the screw in the second, opposite direction. In some embodiments, the freewheel capability of the electric ratchet also provides some small level of motor power to offset drive train drag when the motor is rotated in the second freewheel direction. Accordingly, in some examples, where the drive train drag exceeds the frictional force on the surgical hardware (such as a bone screw), the hardware still will not rotate with the driver in both the first driving and second freewheeling directions. Instead, it will rotate with the driver in the first driving direction, but the motor will operate to offset the inherent drag in the driver so that the driver does not rotate with the driver in the second freewheel direction. This provides the user with the perception that the electric ratcheting function is freewheel rotating in the second freewheel direction, although the drag forces are being overcome by the motor.

The devices, systems, and methods described herein provide an improved system of driving surgical tools, such as bone anchors and other surgical tools. Applicants note that the procedures disclosed herein are merely exemplary and that the systems and methods disclosed herein may be utilized for numerous other medical processes and procedures. Although several selected embodiments have been illustrated and described in detail, it will be understood that they are exemplary, and that a variety of substitutions and alterations are possible without departing from the spirit and scope of the present invention, as defined by the following claims.

What is claimed is:

1. A driver comprising:
a housing having a handle portion;
a motor disposed within the housing, wherein the motor comprises a stator and a rotor;
a power source configured to supply power to the motor; and
a controller configured to control the motor to operate as an electric ratchet, wherein the controller is configured to, while controlling the motor to operate as an electric ratchet,
commutate the motor to maintain a rotational position of the rotor relative to the stator while the housing is being rotated in a first direction relative to one of the stator and the rotor, and
permit freewheel displacement of the rotor relative to the stator while the housing is being rotated in a second direction relative to the one of the stator and the rotor, wherein the second direction is opposite the first direction.

2. The driver of claim 1, wherein the controller is configured to:
while commutating the motor to maintain the rotational position of the rotor relative to the stator, prevent the rotor from rotating relative to the stator in the first direction; and
while permitting freewheel displacement of the rotor, permit the rotor to rotate relative to the stator in the second direction.

3. The driver of claim 1, wherein the controller is configured to:
commutate the motor to maintain the rotational position of the rotor relative to the stator while loading is applied in the second direction on the motor; and
permit freewheel displacement of the rotor relative to the stator while loading is applied in the first direction on the motor.

4. The driver of claim 1, wherein the rotor is disposed within the stator.

5. The drive of claim 1, wherein:
the controller is configured to operate the motor as the electric ratchet while at least one of (i) the motor is powered off, (ii) a shaft is not being driven by the motor, or (iii) the motor is powered to provide an output torque that matches an amount of torque to offset drag of a drivetrain; and
the shaft is connected to the rotor.

6. The driver of claim 1, wherein:
the housing or the stator is unable to rotate relative to the rotor in the second direction while the controller is commutating the motor to maintain the rotational position of the rotor relative to the stator; and
the housing or the stator is able to rotate relative to the rotor in the first direction while the controller is permitting freewheel displacement of the rotor.

7. The driver of claim 1, wherein the controller is configured to:
estimate a starting position of the rotor relative to the stator;
position the rotor relative to the stator at the starting position;
commutate the motor to maintain the rotor at the starting position relative to the stator while offset loading is applied on the motor in the second direction; and
permit displacement of the rotor relative to the stator to a second position relative to the stator in response to loading applied on the motor in the first direction.

8. The driver of claim 7, wherein the controller is configured to:
determine an error factor as a difference between the start position and a current position of the rotor; and
commutate the motor to maintain the start position if the error factor exceeds a predetermined threshold.

9. The driver of claim 7, wherein the controller is configured to subsequent to permitting displacement of the rotor relative to the stator to the second position, commutating the motor to maintain the rotor at the second position relative to the stator while offset loading is applied on the rotor in the second direction.

10. The driver of claim 9, wherein the controller is configured to:
determine an error factor as a difference between the second position and a current position of the rotor; and
commutate the rotor to maintain the second position if a difference between the current position and the second position exceeds a predetermine threshold.

11. A method comprising:
supplying power to a motor, wherein the motor is disposed within a housing of a hand tool, and wherein the motor comprises a stator and a rotor; and
controlling the motor to operate as an electric ratchet, wherein the controlling of the motor comprises
commutating the motor to maintain a rotational position of the rotor relative to the stator while the housing is being rotated in a first direction relative to one of the stator and the rotor, and
permitting freewheel displacement of the rotor relative to the stator while the housing is being rotated in a second direction relative to the one of the stator and the rotor, wherein the second direction is opposite the first direction.

12. The method of claim 11, further comprising:
while commutating the motor to maintain the rotational position of the rotor relative to the stator, preventing the rotor from rotating relative to the stator in the first direction; and
while permitting freewheel displacement of the rotor, permitting the rotor to rotate relative to the stator in the second direction.

13. The method of claim 11, further comprising:
commutating the motor to maintain the rotational position of the rotor relative to the stator while loading is applied in the second direction on the motor; and
permitting freewheel displacement of the rotor relative to the stator while loading is applied in the first direction on the motor.

14. The method of claim 11, wherein:
while commutating the motor to maintain the rotational position of the rotor relative to the stator, the housing or the stator is unable to rotate relative to the rotor in the second direction; and
while permitting freewheel displacement of the rotor, the housing or the stator is able to rotate relative to the rotor in the first direction.

15. The method of claim 11, further comprising:
estimating a starting position of the rotor relative to the stator;

positioning the rotor relative to the stator at the starting position;

commutating the motor to maintain the rotor at the starting position relative to the stator while offset loading is applied on the motor in the second direction; and permitting displacement of the rotor relative to the stator to a second position relative to the stator in response to loading applied on the motor in the first direction.

16. A method of operating a driver, the method comprising:

providing power from a power source to a motor, wherein the motor is within the driver, and wherein the motor comprises a stator and a rotor; and controlling the motor to operate as an electric ratchet including commutating the motor to maintain a rotational position of the rotor relative to the stator while loading is applied in a first direction on the motor, and permitting freewheel displacement of the rotor relative to the stator while loading is applied in a second direction on the motor, wherein the second direction is opposite the first direction.

17. The method of claim 16, wherein:

the driver is within a housing of a hand tool; and the rotor is disposed within the stator.

18. The method of claim 16, further comprising:

receiving signals indicative of a location of the rotor relative to the stator; and based on the received signals, powering the motor to maintain the rotational position of the rotor relative to the stator.

19. The method of claim 18, wherein the signals are indicative of an electromagnetic force of the motor or are generated by rotor sensing elements.

20. The method of claim 16, wherein the operating of the motor as the electric ratchet comprises commutating the motor, while torque is applied in the first direction against the rotor, to maintain the rotor at the rotational position.

21. The method of claim 20, wherein the operating of the motor as the electric ratchet permits freewheel displacement of the rotor while torque is applied in the second direction against the rotor.

22. The method of claim 16, further comprising:

while commutating the motor to maintain the rotational position of the rotor relative to the stator, preventing the rotor from rotating relative to the stator in the second direction; and while permitting freewheel displacement of the rotor, permitting the rotor to rotate relative to the stator in the first direction.

23. The method of claim of claim 16, further comprising operating the motor as the electric ratchet while at least one of (i) the motor is powered off, (ii) a shaft is not being driven by the motor, or (iii) the motor is powered to provide an output torque that matches an amount of torque to offset drag of a drivetrain.

24. The method of claim 23, wherein the shaft is connected to the rotor.

25. The method of claim 16, further comprising:

while commutating the motor to maintain the rotational position of the rotor relative to the stator, a housing of the driver or the stator is unable to rotate relative to the rotor in the first direction; and while permitting freewheel displacement of the rotor, the housing of the driver or the stator is able to rotate relative to the rotor in the second direction.

* * * * *